United States Patent [19]

Sherrod et al.

[11] Patent Number: 4,973,325

[45] Date of Patent: Nov. 27, 1990

[54] ABSORBENT ARTICLE HAVING A FLUID TRANSFER MEMBER

[75] Inventors: Earle H. Sherrod, Appleton; Frederich O. Lassen, Neenah, both of Wis.

[73] Assignee: Kimberly-Clark Corporation, Neenah, Wis.

[21] Appl. No.: 328,405

[22] Filed: Mar. 24, 1989

Related U.S. Application Data

[63] Continuation-in-part of Ser. No. 123,483, Nov. 20, 1987, abandoned.

[51] Int. Cl.⁵ .................................................. A61F 13/15
[52] U.S. Cl. .................................. 604/368; 604/378; 604/384; 604/385.1
[58] Field of Search ........................ 604/378, 385.1, 375, 604/374, 367, 384

[56] References Cited

U.S. PATENT DOCUMENTS

| | | | |
|---|---|---|---|
| 810,119 | 6/1906 | Green | 604/378 |
| 3,494,362 | 6/1969 | Burgeni | 128/290 |
| 3,736,931 | 6/1973 | Glassman | 128/290 |
| 3,768,480 | 10/1973 | Mesek | 128/287 |
| 3,888,275 | 6/1975 | Cook | 128/296 |
| 3,903,890 | 9/1975 | Mesek | 128/287 |
| 3,954,107 | 5/1976 | Chesky et al. | 604/385.1 |
| 4,029,101 | 6/1977 | Chesky | 128/290 |
| 4,333,462 | 6/1982 | Holtman et al. | 128/287 |
| 4,531,945 | 7/1985 | Allison | 604/378 |
| 4,559,051 | 12/1985 | Hanson | 604/385 |
| 4,624,666 | 11/1986 | DePossett et al. | 604/378 |
| 4,643,727 | 2/1987 | Rosenbaum | 604/369 |
| 4,678,464 | 7/1987 | Holtman | 604/385 |
| 4,795,453 | 1/1989 | Wolfe | 604/385.1 |
| 4,846,813 | 7/1989 | Raley | 604/378 |

FOREIGN PATENT DOCUMENTS

| | | | |
|---|---|---|---|
| 869206 | 6/1989 | Canada | 604/378 |
| 152972 | 6/1989 | Fed. Rep. of Germany | 604/378 |

*Primary Examiner*—Randall L. Green
*Assistant Examiner*—Robert Clarke
*Attorney, Agent, or Firm*—Thomas J. Connelly

[57] ABSTRACT

An absorbent article is disclosed having a pair of absorbents positioned adjacent to each other. Each absorbent has a first surface facing the body of a user and a second surface aligned opposite to the first surface. A fluid-impermeable baffle is positioned adjacent to the second surface of each absorbent and extends upward around a portion of the absorbents. A fluid permeable cover is positioned adjacent to the first surface of each absorbent and can be sealed to the baffle. The absorbent article further includes a transfer member for facilitating movement of body fluids from the cover downward and outward to distant areas of the absorbents. The transfer member is positioned above, between and below at least a portion of the absorbents and is coaxially aligned the the longitudinal central axis of the article. The transfer member is also spaced apart from the periphery of the absorbents.

39 Claims, 5 Drawing Sheets

ABSORBENT ARTICLE HAVING A FLUID TRANSFER MEMBER

This application is a continuation in part of application Ser. No. 07/123,483 dated Nov. 20, 1987 abandoned.

FIELD OF THE INVENTION

This invention relates to an absorbent article, such as a sanitary napkin, which has a transfer member for facilitating movement of body fluids away from the cover and down into the absorbent.

BACKGROUND OF THE INVENTION

Presently, commercially available absorbent articles, such as diapers, sanitary napkins and incontinent garments, etc., are provided with more absorbent capacity than is normally utilized. For feminine pads in particular, menstrual fluid, as well as other body fluids, tend to be distributed in the mid portion of the pad just under the top cover. The body fluid passes through the cover then and into the absorbent below. When the absorbent is a cellulose fluff, the fluid tends to wet the fluff at the top surface and this decreases the ability of additional fluid to flow downward and outward to the distant areas of the absorbent. As this occurs, additional fluid that impinges on the pad tends to wick sideways and leak off the edges of the pad rather than going down into the absorbent. Any fluid that pools in the mid portion of the pad is likely to leak off the edge should the pad become deformed or distorted by movement of the wearer.

A second problem with conventional absorbent articles, especially incontinent garments, is that if body fluids, such as urine, is applied to the article at a rapid rate, the article is unable to absorb the fluid quick enough. This unabsorbed fluid has a tendency to pool on top of the absorbent and can leak off the sides of the article. Such leakage is unacceptable to the user.

Several attempts at solving the two above-identified problems have been proposed by the following patents:

U.S. Pat. No. 4,531,945 issued to Allison is entitled "Multi Layer Sanitary Appliance". This patent teaches a sanitary napkin which is provided with at least three layers of absorbent material, with the first and third layers being substantially identical. The first and third layers have areas which are in contact with each other, to allow the fluid to pass downward into the absorbent.

U.S. Pat. No. 4,333,462 issued to Holtman et al. is entitled "Absorbent Structure Containing Superabsorbent". This patent teaches an absorbent structure containing superabsorbent. The article uses an absorbent batt positioned between a permeable cover and an impermeable backing member. The absorbent batt contains two reservoirs each formed by compression of the fibers in the reservoir zone. The first reservoir is open towards the cover and the second reservoir is located below the first reservoir and contains particles of superabsorbent.

U.S. Pat. No. 4,559,051 issued to Hanson is entitled "Disposable Incontinence Diaper". This patent teaches a disposable incontinent diaper. The diaper includes a waterproof barrier formed as a flattened bag and having a single opening located adjacent the perineal area of the body of the wearer. Two layers of filler material are positioned within the barrier bag. The upper layer adjacent the opening is a wicking material, while the lower layer is a superabsorbent material.

U.S. Pat. No. 4,029,101 issued to Chesky et al. is entitled "Absorbent Article". This patent teaches an absorbent article for the perineum. The article is an elongated absorbent pad assembly having a front surface for facing the perineum, a back surface, and separable side portions formed adjacent the front surface of the pad assembly. The side portions define a longitudinally extending channel adjacent the lateral mid-point of the pad assembly. The side portions separate during use to expose an increase area of the pad assembly.

While the above-identified products attempt to alleviate the above two mentioned problems, there is still a need for an absorbent article that has a greater ability to distribute impinging body fluids to a greater area of the absorbent material. Furthermore, there is a need for an absorbent article which will resists side leakage if the pad is twisted or distorted and is better capable of resisting bending and twisting when the article is being worn by the wearer.

SUMMARY OF THE INVENTION

Briefly, the present invention relates to an absorbent article such as a feminine pad, a diaper, an incontinent garment, etc. The absorbent article contains a pair of absorbents positioned adjacent to each other. Each absorbent has a first surface facing the body of the user and a second surface aligned opposite to the first surface. A fluid-impermeable baffle is positioned adjacent to the second surface of each absorbent and extends upward around a portion of the absorbents. A fluid permeable cover is positioned adjacent to at least the first surface of each of the absorbents. The absorbent article also contains a transfer member for facilitating movement of body fluid from the cover downward and outward to distant areas of the absorbents. The transfer member is positioned above, between and below at least a portion of each absorbent and is coaxially aligned with the longitudinal central axis of the article. The transfer member has a length of between about $\frac{1}{2}$ to $\frac{2}{3}$ the overall length of the article and is spaced apart from the periphery of the absorbents.

The general object of this invention is to provide an absorbent article with a transfer member which has the ability to move impinging fluid into contact with a greater area of the absorbent. A more specific object of this invention is to provide a feminine pad with a unique transfer member which can rapidly distribute body fluid which impinges upon it to distant areas of the absorbent.

Another object of this invention is to provide a sanitary napkin which is easy to form and inexpensive to manufacture.

Still, another object of this invention is to provide an absorbent article with a transfer member which provides integrity to the article and assists in preventing deformation of the article once the absorbent becomes wet.

Still further, an object of this invention is to provide a more efficient absorbent article such that a greater proportion of the absorbent material can be utilized during use.

Other objects and advantages of the present invention will become more apparent to those skilled in the art in view of the following description and the accompanying drawings.

DETAILED DESCRIPTION OF THE PREFERRED EMBODIMENTS

Figure 1:
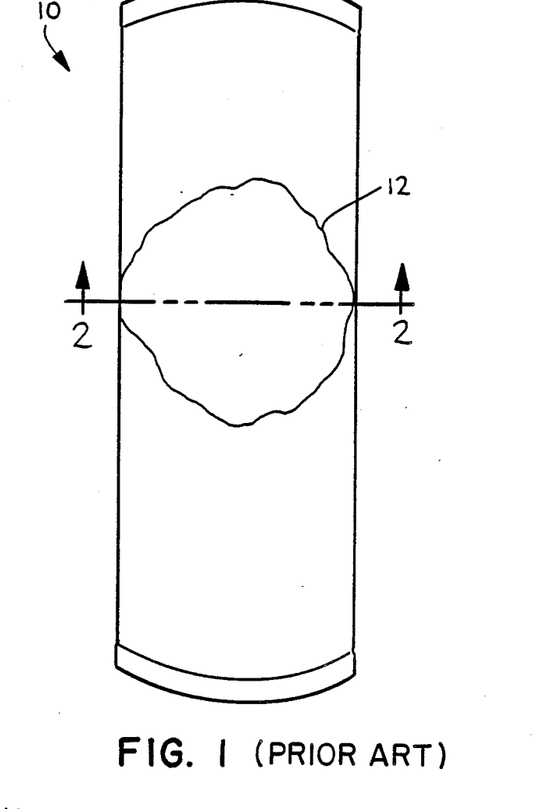
FIG. 1 is a top view of a conventional prior art feminine pad illustrating a stain area located in the mid portion of the pad.
Figure 2:
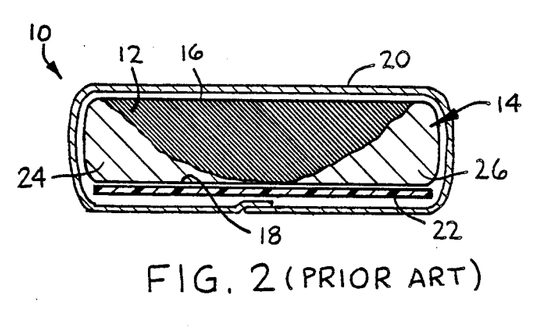
FIG. 2 is a cross-sectional view of the prior art pad shown in FIG. 1 taken along line 2—2 and shows that only a portion of the absorbent is actually utilized for absorbing body fluids.
Figure 3:
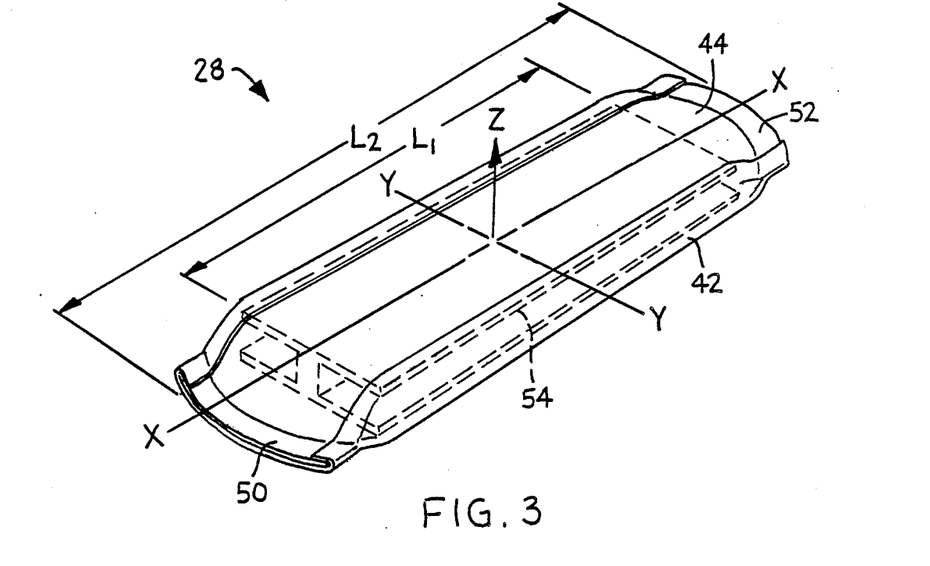
FIG. 3 is a perspective view of a feminine pad incorporating a transfer member located along the longitudinal central axis thereof and having a length of between about ½ to ⅔ the overall length of the pad.
Figure 4:
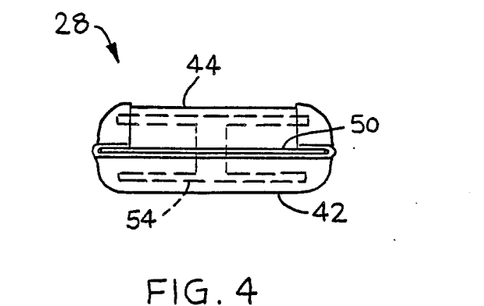
FIG. 4 is an end view of the pad shown in FIG. 3.
Figure 5:
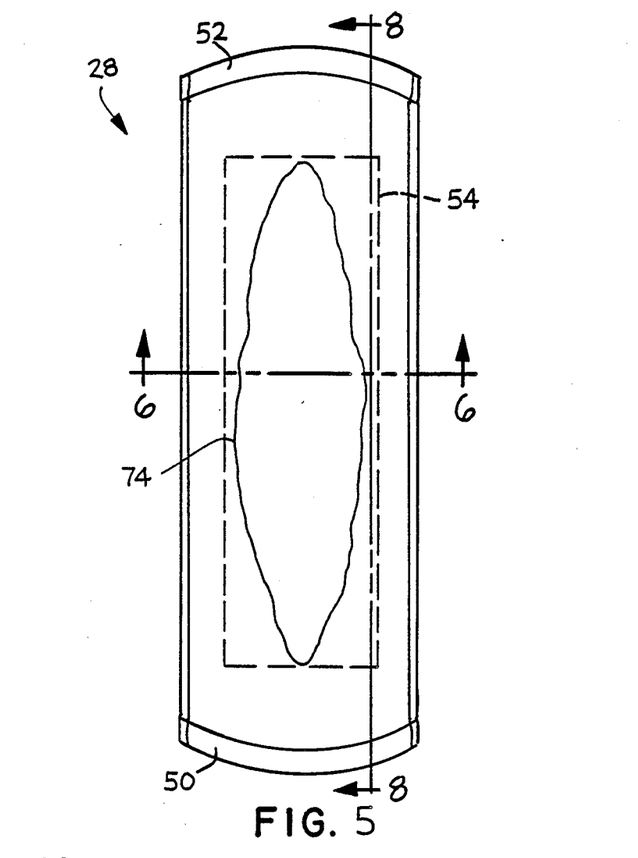
FIG. 5 is a top view of the feminine pad shown in FIG. 3 illustrating the transfer member by dash lines and having an elongated stain pattern.

Referring to FIGS. 1 and 2, a conventional prior art feminine pad 10, also referred to as a sanitary napkin, is shown having a body fluid stain 12 located in the mid portion thereof.

Referring to FIG. 2, the feminine pad 10 is constructed of an absorbent 14, such as cellulose fluff having a top surface 16 and a bottom surface 18. The absorbent 14 is sandwiched between a fluid permeable cover 20 and a fluid-impermeable baffle 22. The body stain 12 tends to pool in the mid portion of the pad at the point where the fluid impinges upon the cover 20. The body fluid will penetrate downward and outward, to a limited extent, into the absorbent 14 in a semi spherical configuration. However, it is very clear from FIG. 2 that distant areas 24 and 26 of the absorbent 14 will not receive any body fluid. One reason for this is that as the absorbent absorbs the body fluid, it becomes wet and the wetness acts as a barrier which prevent additional fluid from penetrating beyond the wet portion to a substantial degree. Accordingly, even though the feminine pad 10 has a sufficient amount of absorbent material to handle a predetermined flow, the pad 10 still fails in actual use because the body fluid cannot penetrate into the absorbent 14 and be transferred to the far reaches of the absorbent 14. Because of this, the fluid tends to pool on the top surface of the absorbent 14 and can leak off the side edges. This leakage is more pronounced in cases where the feminine pad 10 is distorted or twisted by normal body movement.

Referring to FIGS. 3–6, an absorbent article 28 such as a feminine pad, is shown which is constructed of a pair of absorbent 30 and 32 positioned adjacent to each other. The absorbents 30 and 32 each have a first surface 34 and 36, respectively, facing the body of a user and a second surface 38 and 40, respectively, aligned opposite to said first surfaces 34 and 36. The absorbents 30 and 32 can be constructed of a material which exhibits a good liquid holding feature as well as having the capability of absorbing fluid from an adjacent member. Wood fluff, cellulose, gauze and tissue are common absorbent materials. It is also possible to add a superabsorbent to the absorbents 30 and 32 to assist them in retaining body fluid. Another possibility is to form the absorbents 30 and 32 with layers of different densities in order to further segregate absorptive abilities. These various layers could then be reinforced if needed so that the absorbent article 28 maintains its original shape.

Figure 6:
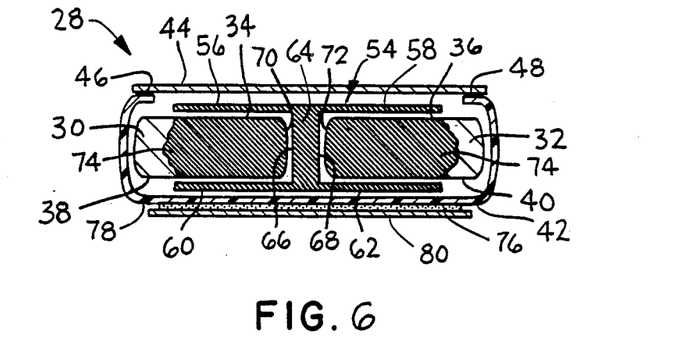
FIG. 6 is a cross-sectional view of the feminine pad shown in FIG. 5 taken along line 6—6 and illustrates the use of an integral H-shaped transfer member.

The absorbent article 28 also includes a fluid-impermeable baffle 42 positioned adjacent to the second surfaces 38 and 40 of each absorbent. The baffle 42 extends upward around a portion of the absorbents 30 and 32 and preferably extends up and covers a small portion of the first surfaces 34 and 36. A fluid permeable cover 44 is positioned adjacent to at least the first surfaces 34 and 36 of each absorbent and can be sealed or otherwise attached to the baffle 42, such as by an adhesive. In FIG. 6, the cover 44 is attached to the baffle 42 by ultrasonic sealing at 46 and 48. Furthermore, two end seals 50 and 52 are formed at opposite ends of the absorbent article 28 to give it an aesthetically pleasing appearance and shape.

A transfer member 54 is positioned within the absorbent article 28 and facilitates movement of body fluid from the cover 44 downward and outward to distant areas of the absorbents 30 and 32. The transfer member 54 can be constructed from any material which will readily transfer fluid as well as having the ability to give the fluid up to a cellulose absorbent or to an absorbent containing a superabsorbent. Various materials include blends of hydrophobic (tending not to combine with water) and hydrophilic (having an affinity for water) fibers, blends of polyesters or other hydrophobic fibers and hydrophilic cellulose fibers $(C_6H_{10}O_5)$ X. More specifically, the transfer member 54 can be a blend of polymer fibers including synthetic fibers such as rayon, a blend of polyester and rayon fibers or a blend of polyester, rayon and polypropylene fibers. The blend should contain some hydrophilic fibers or hydrophilic treated fibers to facilitate the flow of body fluid within the member itself. The hydrophilic fibers will assist in transferring the body fluid into the absorbents 30 and 32. The transfer member 54 can be a bonded carded web, an air-formed web, a coform mixture, a meltblown material or a composite of different materials made by one of many known air forming processes. The transfer member 54 is shown as an integral member which is positioned above, between and below at least a portion of the absorbents 30 and 32. The transfer member 54 is coaxially aligned with the longitudinal central axis of the absorbent article 28 and has a length which is between about ½ to ⅔ the overall length of the article 28, as denoted by $L_1$ and $L_2$. The transfer member 54 is spaced apart from the periphery of the absorbents 30 and 32, and preferably, has a top surface which is shaped as an elongated rectangle. The position and shape of the transfer member 54 facilitates quick and efficient Z-directional movement of the body fluid downward between the absorbents 30 and 32 as well as rapid outward movement in the X and Y directions along the top and bottom surfaces of the absorbents 30 and 32.

The absorbent article 28 has the advantage of having the equivalence of an open area in the middle between the absorbents 30 and 32 which allows it to flex in the middle. This enables the absorbent article to conform to the wearer's body thereby reducing bunching and twisting. The ability to flex in the middle also allows the middle portion to lift upward for better contact with the wearer's body. This upward flexing positions the transfer member 54 to receive the initial flow of the body fluid. The transfer member 54 can also add integrity to the absorbent article 28 and therefore eliminates the need for a tissue wrap around the absorbents 30 and 32. The transfer member 54 also provides sufficient strength so that the tissue wrap can be eliminated and this can result in a cost savings.

In FIG. 6, the transfer member 54 is depicted as an H-shaped member laid horizontally relative to the absorbents 30 and 32. The H-shaped transfer member 54 has a pair of first legs 56 and 58 and a pair of second legs 60 and 62 joined together by a transverse beam 64. The transverse beam 64 is aligned perpendicular to the cover 44 and preferably is coaxially aligned with the longitudinal central axis of the absorbent article 28. The pair of first legs 56 and 58 are positioned parallel to the first surfaces 34 and 36 of the absorbents, while the pair of second legs 60 and 62 are positioned parallel to the second surfaces 38 and 40 of the absorbents. The pair of first and second legs 56 & 58 and 60 & 62, respectively, will contact a substantial portion of the first and second surfaces 34 & 36 and 38 & 40, respectively, of the absorbents 30 and 32. Likewise, the transverse beam 64 has opposite side surfaces 66 and 68 which will be in direct contact with side surfaces 70 and 72 of the absorbents 30 and 32 respectively. It should be noted that in FIG. 6, the various structural elements are shown as being spaced apart for visually understanding only. In reality, the various elements of the absorbent article 28 will be in direct contact with adjacent members. In particular, the transfer member 54 is in direct contact with the absorbents 30 and 32 so as to facilitate movement of body fluid therebetween.

The H-shaped transfer member 54 is laid horizontally within the feminine pad 28 and surrounds a substantial portion of the surface area of the absorbents 30 and 32. In this horizontal alignment, the beam 64 is positioned perpendicular to the cover 44 and has a width which is greater than the thickness of either pair of legs. The beam 64 also has a height, i.e. its vertical dimension, which is greater than the thickness of either pair of legs. The width and height of the beam 64 should be dimensioned so as to rapidly and efficiently facilitate movement of body fluid, which impinges on the central portion of the cover 44, downwards and outwards into the absorbents 30 and 32. The width of the beam 64 is important for one can design the width to correspond to the type of flow which one envisions will impinge on the absorbent article 28. By making the transverse beam 64 wider, more body fluid can be quickly drawn downward to the second legs 60 and 62 and then lengthwise and horizontally along the X and Y axes, respectively, to the underside of the absorbents 30 and 32. Simultaneously, additional fluid impinging on the transfer member 54 will be drawn outwardly in the X and Y direction by the first legs 56 and 58 so that it can be transferred to the upper surface of the absorbents 30 and 32. In so doing, a greater proportion of body fluid can be quickly absorbed by the absorbents 30 and 32 even when they are constructed of a material and are sized identical to prior art products.

Referring back to FIG. 5, the presence of the transfer member 54 creates a body fluid stain 74 which is distributed along the longitudinal axis of the absorbent article 28. The body fluid is also distributed to a greater portion of the distant areas of the absorbents 30 and 32 as is clearly shown in FIG. 6.

Referring again to FIG. 6, the absorbent article 28 further contains a garments adhesive 76 which is attached to a lower surface 78 of the baffle 42. A removable peel strip 80 is applied to the outside of the garment adhesive 76 and is designed to be removed by the wearer before the article 28 is to be worn. Normally, the wearer will remove the peel strip 80 and attach the absorbent article 28, via the garment adhesive 76 to the inside of her undergarment. The undergarment will then be pulled up to her crotch such that the absorbent article, i.e. feminine pad, is positioned relative to her perineum.

Figures 7, 8:
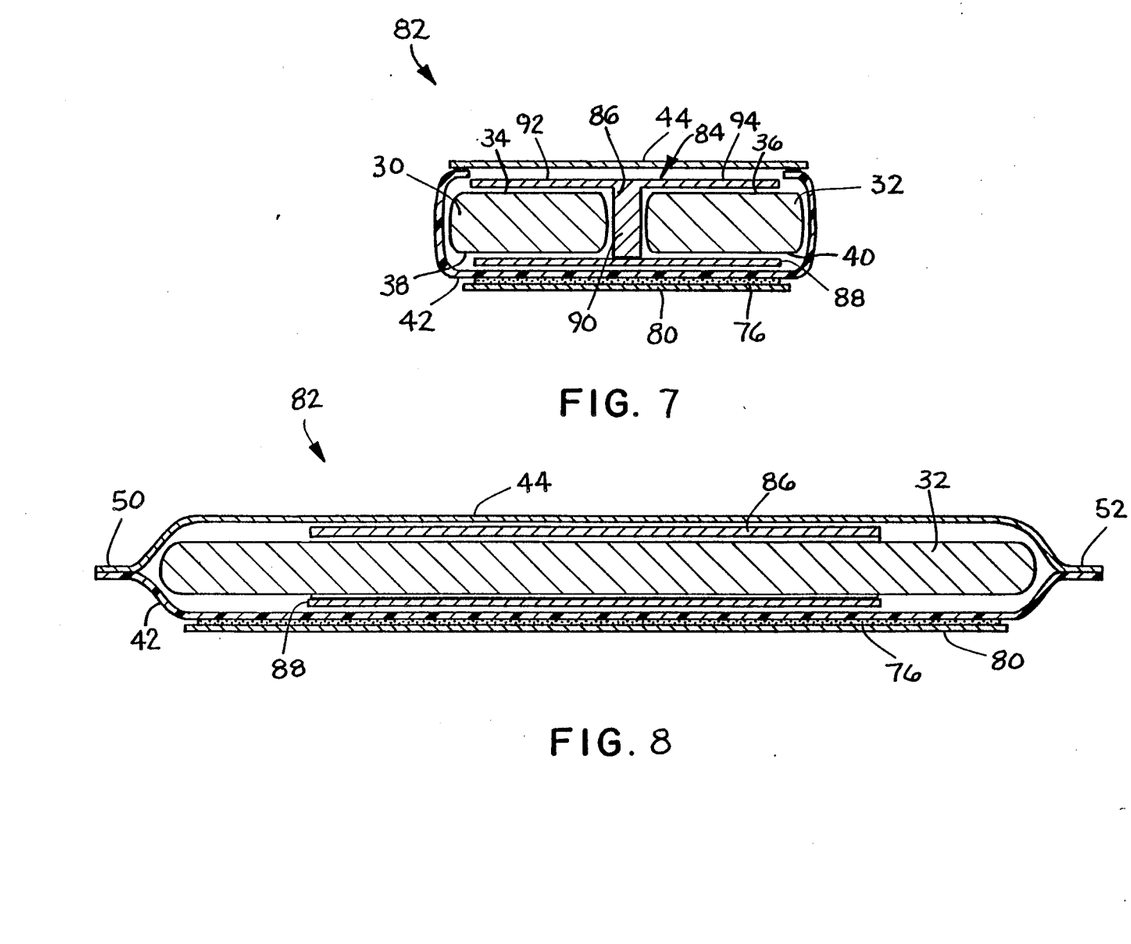
FIG. 7 is a cross-sectional view of a feminine pad utilizing a two component transfer member.
FIG. 8 is a cross-sectional view of the feminine pad shown in FIG. 5 taken along line 8—8 and illustrates the transfer member as having a length of between about ½ to ⅔ the overall length of the pad.

Referring to FIGS. 7 and 8, a feminine pad 82 is shown which incorporates a bicomponent transfer member 84. It should be noted that structural elements identical to those shown in FIG. 6, bear the same reference numerals. The transfer member 84 includes a first member 86 and a second member 88. The first member 86 is T-shaped in cross section and has a vertical column 90 which is positioned between the absorbents 30 and 32. A pair of arms 92 and 94 extend horizontally outward from the column 90 and contact a substantial portion of the first surfaces 34 and 36 of the absorbents 30 and 32, respectively. The second member 88 is a substantially flat rectangular member which is positioned adjacent to the second surfaces 38 and 40 of the absorbents 30 and 32, respectively. The second member 88, like the first member 86, extends horizontally outward and contacts a substantial portion of the second surfaces 38 and 40. The transfer member 84 does not extend to the periphery of the absorbents 30 and 32 but, has an overall length which is between about $\frac{1}{2}$ to $\frac{2}{3}$ the overall length of the entire pad 82. This feature is best illustrated in FIG. 8. By constructing the transfer member 84 so that it has a smaller surface area than the combined surface area of the absorbents 30 and 32, one can be assured that body fluid impinging on the pad 82 will be moved outward but not into contact with the periphery of the pad 82. The body fluid will be brought into contact with a greater surface area of the absorbents 30 and 32 and can then be absorbed therein. If the absorbents 30 and 32 exhibit any wicking action, the liquid will be drawn into the outer reaches of the absorbents 30 and 32 but the size dimension between the transfer member 84 and the absorbents 30 and 32 will provide adequate distance to insure that no body fluid will leak off the sides or ends of the pad 82. The transfer member 84 is preferably coaxially aligned with the longitudinal central axis of the pad 82. In this position, it acts to direct and distribute body fluid downward into the absorbents 30 and 32 as well as lengthwise along the longitudinal axis.

As depicted in FIGS. 7 and 8, the thickness of the second member 88 is essentially equal to the thickness of the arms 92 and 94 of the first member 86. However, it is possible to utilize a second member 88 which is thinner or thicker than the arms 92 and 94 of the first member 86, if such is advantageous to a particular product. For example, in a diaper and incontinent garment, it may be advantageous to employ a thicker second member 88 such that urine can quickly pass down through the column 90 and then horizontally along the second member 88 so that it can be absorbed into the absorbents 30 and 32. This will convey a drier feeling to the wearer. On the other hand, for a product such as a sanitary napkin, it may be more advantageous to employ a thicker first member 86 since menses and other viscous body fluid discharged by the body may not flow readily. Therefore, it might be more advantageous to move this body fluid horizontally outward by the transfer member 84 so that it can be absorbed into the top surface of the absorbents 30 and 32.

Figure 9:
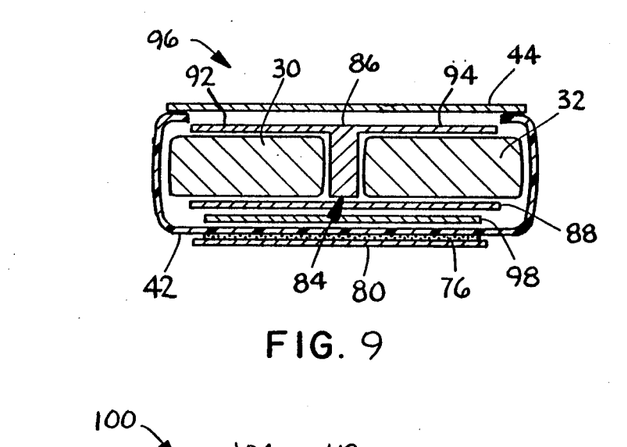
FIG. 9 is a cross-sectional view of a feminine pad having a two component transfer member with a liquid storage layer positioned below the transfer member.

Referring to FIG. 9, a feminine pad 96 is depicted which is similar to that shown in FIG. 7, except that a fluid retention member 98 is positioned between the second member 88 and the baffle 42. The fluid retention member 98 can be a sheet of absorbent such as a microfiber sheet, a sheet of superabsorbent material, or a carrier sheet for superabsorbent particles. The fluid retention member 98 can have a thickness which is equal to, less than or greater than the thickness of the second member 88. However, in certain instances, depending upon the type of material and its mechanism of transferring or absorbing body fluids, it may be advantageous to use a thin second member 88 and a thicker fluid retention member 98. The thin second member 88 has the capability of facilitating movement of body fluid across its surface area but will not retain the fluid. This body fluid is then absorbed by either the absorbents 30 and 32 or by the fluid retention member 98. The presence of the fluid retention member 98 is particularly advantageous when the flow is slow because it usually has a great fluid retention feature but is not capable of rapidly absorbing fluid. The fluid retention member 98 can, to a certain degree, pull body fluids out of the absorbents 30 and 32 and retain them when the second member 88 is very thin.

The fluid retention member 98 can contain superabsorbents which are very good at retaining body fluid. Superabsorbents are generally hydrocolloidal polymers that have the ability to absorb a great amount of fluid in relation to their own weight. Typical superabsorbents used in diapers, incontinent garments and feminine products, can absorb anywhere from 5 to 30 times their weight in fluid. However, the absorption mechanism is not a rapid adsorption and is usually slower than the rate of fluid absorption by cellulose fluff material. The placement of the fluid retention member 98 at the bottom of the pad away from the body of the user allows additional time for the superabsorbents to absorb fluid from the transfer member 84.

Figure 10:
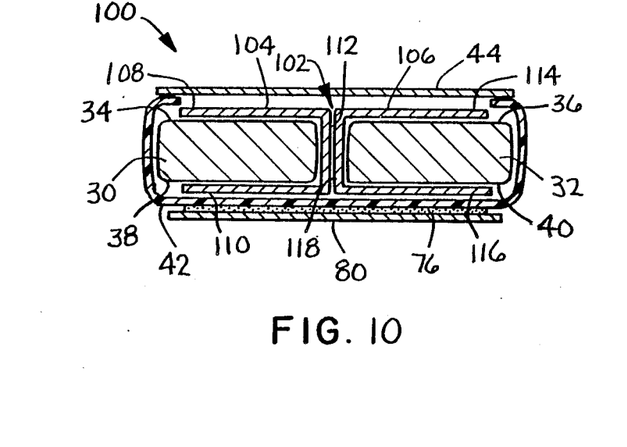
FIG. 10 is a cross-sectional view of an alternative feminine pad wherein the transfer member consists of two "U" shaped members positioned back-to-back.

Referring to FIG. 10, an alternative embodiment for a feminine pad 100 is illustrated which is similar to FIG. 6, except that a transfer member 102 is shown which includes a pair of U-shaped members 104 and 106. The U-shaped member 104 has first and second legs 108 and 110, respectively, joined together by a transverse beam 112. The second U-shaped member 106 has first and second legs 114 and 116, respectively, joined by a transverse beam 118. The two U-shaped members 104 and 106 are positioned back-to-back such that the transverse beams 112 and 118 contact each other. The first and second legs 108 & 114 and 110 & 116, respectively, will extend horizontally outward and contact a substantial portion of the first and second surfaces 34 & 36 and 38 & 40, respectively, of the absorbents 30 and 32. The outer periphery of the U-shaped members 104 and 106 will be spaced apart from the outer peripheries of the absorbents 30 and 32. This assures that fluid transferred through the U-shaped members 104 and 106 will not be in direct contact with the outside material of the pad 100. Each U-shaped members 104 and 106 can be an integral member, as is shown in FIG. 10, or they can be constructed of separate individual members as shown in FIG. 11.

In FIG. 10, the first legs 108 and 114 are positioned parallel to the first surfaces 34 and 36 of the absorbents 30 and 32, while the second legs 110 and 116 are positioned parallel to the second surfaces 38 and 40 of the absorbents 30 and 32. When this occurs, the transverse beams 112 and 118 will be positioned approximately perpendicular to the cover 44. It should be noted that the transverse beams 112 and 118 of the "U" shaped members 104 and 106, respectively, each has a width approximately equal to the thickness of either the first or second legs 108 & 114 and 110 & 116, respectively. These dimensions assures that each U-shaped member can be made out of a standard thickness web and can be sized and dimensioned such that the U-shaped member fits a particular product. It should also be noted that the vertical height or length of each of the transverse beams 112 and 118 as depicted in FIG. 10, will be greater than the thickness of either absorbent 30 or 32. By so dimensioning the transverse members 112 and 118, one can be assured that the transfer member 102 will fit snugly about the absorbents 30 and 32 without necessarily compressing the absorbents during the assembly process. The compression of absorbents 30 and 32 could detrimentally affect their ability to accept a fluid in a timely manner.

Figure 11:
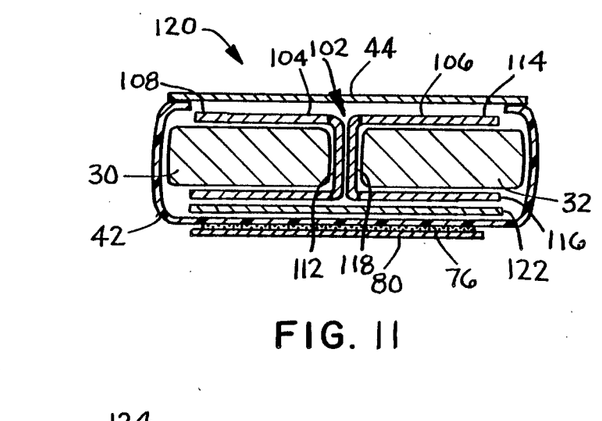
FIG. 11 is a cross-sectional view of another embodiment using a pair of "U" shaped transfer members with a liquid storage layer positioned below the transfer members.

Referring to FIG. 11, an alternative feminine pad 120 is depicted which is similar in all aspects to FIG. 10, except for two features. First, the transfer member 102 is shown being constructed of individual members. Second, a fluid retention member 122 is positioned between the second legs 110 and 116 of the U-shaped members 104 and 106, respectively, and the baffle 42. The fluid retention member 22 is similar to the fluid retention member 98 which was explained above.

Figure 12:
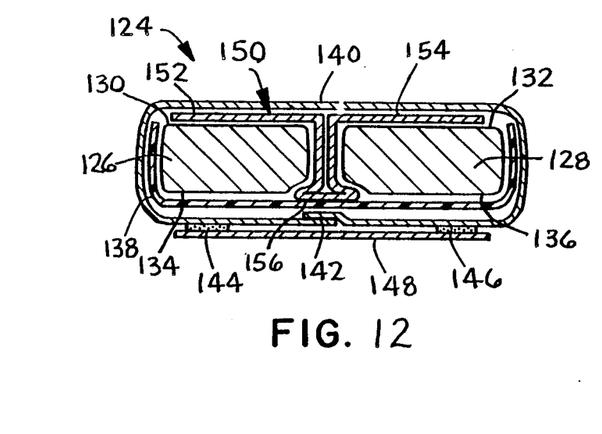
FIG. 12 is a cross-sectional view of yet another embodiment wherein an integral transfer member is utilized. In this embodiment the cover also completely surrounds the absorbent as well as the fluid impermeable baffle.

Referring to FIG. 12, an alternative feminine pad 124 is illustrated having a pair of absorbents 126 and 128 each having a first surface 130 and 132, respectively, and a second opposite surface 134 and 136, respectively. A fluid-impermeable baffle 138 is positioned adjacent to the second surfaces 134 and 136, and extends upward and around a portion of each of the absorbents 126 and 128. A fluid permeable cover 140 is wrapped around the entire pad 124 and overlaps itself and is attached by an adhesive connection at 142. A pair of garment adhesive strips 144 and 146 are attached to the underside of the pad 124 against the wrap cover 140 and retain a removable peel strip 148 which is designed to be discarded when the pad 124 is ready to be used. The pad 124 also contains an integral transfer member 150 formed of a flexible web of material having a constant cross-sectional thickness. The transfer member 150 is folded into a unique shape, much like and I-beam such that it is positioned above, between and below at least a portion of the absorbents 126 and 128. The transfer member 150 has two horizontal arms 152 and 154, which are joined by a central portion 156 which is positioned between and below the absorbents 126 and 128. The central portion 156 is folded and facilitates movement of body fluids downward and outward into the bottom portion of the absorbents 126 and 128, although not to the same extent as the H-shaped or U-shaped members described earlier. It is also possible to use a fluid retention member in combination with the transfer member 150.

While the invention has been described in conjunction with several specific embodiments, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

We claim:

1. An absorbent article comprising:
   (a) a pair of absorbents positioned adjacent to each other, each absorbent having a first surface facing the body of a user and a second surface aligned opposite to said first surface;
   (b) a fluid-impermeable baffle positioned adjacent to said second surface of each absorbent and extending upward around a portion of said absorbents;
   (c) a fluid permeable cover positioned adjacent to at least said first surface of each of said absorbents; and
   (d) transfer means for facilitating movement of body fluid from said cover downward and outward to distant areas of said absorbents, said transfer means being positioned above, between and below at least a portion of said absorbents and coaxially aligned with the longitudinal central axis of said article while being spaced apart from the periphery of said absorbents.

2. The absorbent article of claim 1 wherein said transfer means is an integral member.

3. The absorbent article of claim 1 wherein a fluid retention member is positioned between a bottom surface of said transfer means and said baffle.

4. The absorbent article of claim 3 wherein said fluid retention member contains a superabsorbent.

5. An absorbent article comprising:
   (a) a pair of absorbents positioned adjacent to each other, each absorbent having a first surface facing the body of a user and a second surface aligned opposite to said first surface;
   (b) a fluid-impermeable baffle positioned adjacent to said second surface of each absorbent and extending around said absorbents and partially covering said first surfaces;
   (c) a fluid permeable cover positioned adjacent to said first surface of each of said absorbents and attached to said baffle; and
   (d) transfer means for facilitating movement of body fluid from said cover downward and outward to distant areas of said absorbents, said transfer means being an H shaped member laid horizontally and contacting a substantial portion of said first and second surfaces of said absorbents.

6. The article of claim 5 wherein said transfer means has first and second legs joined by a transverse beam, said transverse beam being aligned perpendicular to said cover.

7. The article of claim 5 wherein said transfer means is coaxially aligned with the longitudinal central axis of said article while being spaced apart from the periphery of said absorbents.

8. The article of claim 6 wherein said first leg is positioned parallel to said first surface of each of said absorbents and said second leg is positioned parallel to said second surface of each of said absorbents.

9. The article of claim 6 wherein said transverse beam has a width greater than the thickness of either of said legs.

10. The article of claim 6 wherein said transverse beam has a height greater than the thickness of either of said legs.

11. The article of claim 6 wherein a fluid retention member is positioned between said second leg of said transfer means and said baffle.

12. The article of claim 5 wherein said transfer member is formed from a blend of hydrophobic and hydrophilic fibers.

13. The article of claim 12 wherein said hydrophobic fibers are polyester and said hydrophilic fibers are cellulose.

14. The article of claim 5 wherein said transfer member is formed from a blend of polymer fibers including rayon.

15. The article of claim 5 wherein said transfer means is formed from a blend of polyester, rayon and polypropylene fibers.

16. The article of claim 5 wherein said transfer means is a carded web formed of a blend of polyester, rayon and polypropylene fibers.

17. The article of claim 5 wherein said transfer member is an air-formed web.

18. A sanitary napkin for absorption of body fluids comprising:
   (a) a pair of absorbents positioned adjacent to each other, each absorbent having a first surface facing the body of a user and a second surface aligned opposite to said first surface;
   (b) a fluid-impermeable baffle positioned adjacent to said second surface of each of said absorbents and extending upward around a portion of said absorbents;
   (c) a fluid permeable cover positioned adjacent to said first surface of each of said absorbents and attached to said baffle; and
   (d) transfer means for facilitating movement of body fluid from said cover downward and outward to distant areas of said absorbents, said transfer means including a pair of U-shaped members each having first and second legs joined by a transverse beam, said U-shaped members positioned back to back with said beams touching each other and said first and second legs contacting a substantial portion of said first and second surfaces, respectively, of each of said absorbents.

19. The sanitary napkin of claim 18 wherein a fluid retention member is positioned between said second leg of each of said U-shaped members and said baffle.

20. The sanitary napkin of claim 18 wherein said transverse beam of each U-shaped member is positioned approximately perpendicular to said cover.

21. The sanitary napkin of claim 18 wherein each of said U-shaped members is an integral member.

22. The sanitary napkin of claim 18 wherein said first leg of each U-shaped member is positioned parallel to said first surface of each absorbent and said second leg of each U-shaped member is positioned parallel to said second surface of each absorbent.

23. The sanitary napkin of claim 18 wherein said transverse beam of each U-shaped member has a width approximately equal to the thickness of either of said legs.

24. The sanitary napkin of claim 18 wherein the length of each of said transverse beams is greater than the thickness of either of said absorbents.

25. The sanitary napkin of claim 18 wherein said transfer means is formed from a blend of hydrophobic and hydrophilic fibers.

26. The sanitary napkin of claim 25 wherein said hydrophobic fibers are polyester and said hydrophilic fibers are cellulose.

27. The sanitary napkin of claim 18 wherein said transfer means is formed from a blend of polymer fibers including rayon.

28. The sanitary napkin of claim 18 wherein said transfer means is formed from a blend of polyester, rayon and polypropylene fibers.

29. The sanitary napkin of claim 18 wherein said transfer means is a carded web formed of a blend of polyester, rayon and polypropylene fibers.

30. The sanitary napkin of claim 18 wherein said transfer means is an air formed web.

31. An absorbent pad for absorption of body fluids comprising:
(a) a pair of absorbents positioned adjacent to each other, each absorbent having a first surface facing the body of a user and a second surface aligned opposite to said first surface;
(b) a fluid-impermeable baffle positioned adjacent to said second surface of each of said absorbents and extending upward around a portion of each of said absorbents;
(c) a fluid permeable cover positioned adjacent to said first surface of each of said absorbents and attached to said baffle; and
(d) transfer means for facilitating movement of body fluid from a middle portion of said cover downward and outward to distant areas of said absorbents, said transfer means including first and second members, said first member being T shaped and having a column positioned between said absorbents and an adjoining pair of arms contacting a substantial portion of said first surfaces of said absorbents, and a second member positioned adjacent to said second surface of each of said absorbents and in contact with said column.

32. The absorbent pad of claim 31 wherein said transfer means is coaxially aligned with the longitudinal central axis of said pad and is spaced apart from the periphery of said absorbents.

33. The absorbent pad of claim 32 wherein said column is coaxially aligned with the longitudinal central axis of said pad and is spaced apart from the periphery of said absorbents.

34. The absorbent pad of claim 31 wherein a fluid retention member is positioned between said second member and said baffle.

35. The absorbent pad of claim 34 wherein said fluid retention member contains a superabsorbent.

36. The absorbent pad of claim 31 wherein said transfer means has a length about ½ to ⅔ the overall length of said pad.

37. The absorbent pad of claim 31 wherein said second member is thicker than either arm of said first member.

38. An absorbent article comprising:
(a) a pair of absorbents positioned adjacent to each other, each absorbent having a first surface facing the body of a user and a second surface aligned opposite to said first surface;
(b) a fluid-impermeable baffle positioned adjacent to said second surface of each absorbent and extending upward around a portion of each of said absorbents;
(c) a fluid permeable cover positioned adjacent to said first surface of each of said absorbents and completely encircling both said absorbents and said baffle; and
(d) transfer means for facilitating movement of body fluid from said cover downward and outward to distant areas of said absorbents, said transfer means being positioned above, between and below a portion of said absorbents and coaxially aligned with the longitudinal central axis of said article while being spaced apart from the periphery of said absorbents.

39. An absorbent article comprising:
(a) a pair of absorbents positioned adjacent to each other, each absorbent having a first surface facing the body of a user and a second surface aligned opposite to said first surface;
(b) a fluid-impermeable baffle positioned adjacent to said second surface of each absorbent and extending upward around a portion of said absorbents;
(c) a fluid permeable cover positioned adjacent to said first surface of each of said absorbents; and
(d) transfer means for facilitating movement of body fluid from said cover downward and outward to distant areas of said absorbents, said transfer means being coaxially aligned with the longitudinal central axis of said article and having a length which is between about ½ to ⅔ the overall length of said article, said transfer means being positioned above, between and below said pair of absorbents.

* * * * *

UNITED STATES PATENT AND TRADEMARK OFFICE
CERTIFICATE OF CORRECTION

PATENT NO. : 4,973,325

DATED : November 27, 1990

INVENTOR(S) : Earle H. Sherrod; Frederich O. Lassen

It is certified that error appears in the above-identified patent and that said Letters Patent is hereby corrected as shown below:

Title Page:
In the Abstract, line 7, delete the words "fluid permeable" and substitute therefor --fluid-permeable--.

Column 1, line 19, delete the word "tend" and substitute therefor --tends--.

Column 1, line 20, delete the words "mid portion" and substitute therefor --mid-portion--.

Column 1, line 22, delete the words "then and" and substitute therefor --and then--.

Column 1, lines 29 and 30, delete the words "mid portion" and substitute therefor --mid-portion--.

Column 1, line 35, delete the word "is" and substitute therefor --are--.

Column 1, line 36, delete the word "quick" and substitute therefor --quickly--.

Column 1, line 55, after the word "reservoirs" insert --,--.

Column 2, line 10, delete the word "increase" and substitute therefor --increased--.

UNITED STATES PATENT AND TRADEMARK OFFICE
CERTIFICATE OF CORRECTION

PATENT NO. : 4,973,325
DATED : November 27, 1990
INVENTOR(S) : Earle H. Sherrod; Frederich O. Lassen It is certified that error appears in the above-identified patent and that said Letters Patent is hereby corrected as shown below:

Column 2, line 17, delete the word "resists" and substitute therefor --resist--.

Column 2, lines 32 and 33, delete the words "fluid permeable" and substitute therefor --fluid-permeable--.

Column 2, line 55, after the word "Still" delete the comma.

Column 3, lines 4 and 5, delete the words "mid portion" and substitute therefor --mid-portion--.

Column 3, lines 40 and 41, delete the words "fluid impermeable" and substitute therefor --fluid-impermeable--.

Column 3, lines 47 and 48, delete the words "mid portion" and substitute therefor --mid-portion--.

Column 3, line 52, delete the words "fluid permeable" and substitute therefor --fluid-permeable--.

Column 3, line 54, delete the words "mid portion" and substitute therefor --mid-portion--.

Column 3, line 57, delete the words "semi spherical" and substitute therefor --semi-spherical--.

UNITED STATES PATENT AND TRADEMARK OFFICE
CERTIFICATE OF CORRECTION

PATENT NO. : 4,973,325
DATED : November 27, 1990
INVENTOR(S) : Earle H. Sherrod; Frederich O. Lassen It is certified that error appears in the above-identified patent and that said Letters Patent is hereby corrected as shown below:

Column 3, line 60, after the word "that" insert --,--.

Column 3, line 62, delete the word "prevent" and substitute therefor --prevents--.

Column 4, line 6, after the number "28" insert --,--.

Column 4, line 8, delete the word "absorbent" and substitute therefor --absorbents--.

Column 4, lines 24 and 25, delete the words "fluid- impermeable" and substitute therefore --fluid-impermeable--.

Column 4, line 29, delete the words "fluid permeable" and substitute therefor --fluid-permeable--.

Column 4, line 43, after the word "fluid" insert --,--.

Column 4, line 54, delete the words "hydrophilic treated" and substitute therefor --hydrophilic-treated--.

Column 5, line 13, after the word "body" insert --,--.

Column 5, line 44, delete the word "visually" and substitute therefor --visual--.

UNITED STATES PATENT AND TRADEMARK OFFICE
CERTIFICATE OF CORRECTION

PATENT NO. : 4,973,325
DATED : November 27, 1990
INVENTOR(S) : Earle H. Sherrod; Frederich O. Lassen It is certified that error appears in the above-identified patent and that said Letters Patent is hereby corrected as shown below:

Column 5, lines 62 and 63, after the word "important insert --,--.

Column 6, line 17, delete the word "garments" and substitute therefor

--garment--.

Column 6, line 23, after the number "76" insert --,--.

Column 6, line 31, after the number "6" delete the comma.

Column 6, line 46, after the number "32" insert --,--.

Column 6, line 46, after the word "but" delete the comma.

Column 6, line 62, delete the word "insure" and substitute therefor

--ensure--.

Column 7, line 52, after the word "products" delete the comma.

Column 7, line 54, delete the word "adsorption" and substitute therefor

--absorption--.

Column 8, line 12, delete the word "members" and substitute therefor

--member--.

Column 8, line 22, after the word "that" insert --each of--.

Column 8, line 24, delete the word "each".

UNITED STATES PATENT AND TRADEMARK OFFICE
CERTIFICATE OF CORRECTION

PATENT NO. : 4,973,325
DATED : November 27, 1990
INVENTOR(S) : Earle H. Sherrod; Frederich O. Lassen It is certified that error appears in the above-identified patent and that said Letters Patent is hereby corrected as shown below:

Column 8, line 27, delete the word "assures" and substitute therefor

--assure--.

Column 8, line 57, delete the words "fluid permeable" and insert therefor

--fluid-permeable--.

Column 8, line 67, delete the word "and" and substitute therefor --an--.

Claim 1, column 9, line 28, delete the words "fluid permeable" and substitute therefor --fluid-permeable--.

Claim 5, column 9, line 56, delete the words "fluid permeable" and substitute therefor --fluid-permeable--.

Claim 5, column 9, line 62, delete the letter "H" and the word "shaped"

and substitute therefor --H-shaped--.

Claim 18, column 10, line 45, delete the words "fluid permeable" and substitute therefor --fluid-permeable--.

Claim 30, column 11, line 26, delete the words "air formed" and substitute therefor --air-formed--.

Claim 31, column 11, line 37, delete the words "fluid permeable" and substitute therefor --fluid-permeable--.

UNITED STATES PATENT AND TRADEMARK OFFICE
CERTIFICATE OF CORRECTION

PATENT NO. : 4,973,325
DATED : November 27, 1990
INVENTOR(S) : Earle H. Sherrod; Frederich O. Lassen It is certified that error appears in the above-identified patent and that said Letters Patent is hereby corrected as shown below:

Claim 38, column 12, line 25, delete the words "fluid permeable" and substitute therefor --fluid-permeable--.

Claim 39, column 12, line 45, delete the words "fluid permeable" and substitute therefor --fluid-permeable--.

Signed and Sealed this

Sixth Day of October, 1992

Attest:

DOUGLAS B. COMER

Attesting Officer
Acting Commissioner of Patents and Trademarks

UNITED STATES PATENT AND TRADEMARK OFFICE
CERTIFICATE OF CORRECTION

PATENT NO. : 4,973,325

DATED : November 27, 1990

INVENTOR(S) : Earle H. Sherrod; Frederich O. Lassen

It is certified that error appears in the above-identified patent and that said Letters Patent is hereby corrected as shown below:

<u>ON THE TITLE PAGE</u>

In the References Cited, U.S. PATENT DOCUMENTS, line 5, delete patent number "3,888,275" and substitute therefor --3,888,257--.

Signed and Sealed this

Twenty-first Day of September, 1993

Attest:

BRUCE LEHMAN

*Attesting Officer*  *Commissioner of Patents and Trademarks*